(12) United States Patent
Mondi

(10) Patent No.: US 6,533,580 B1
(45) Date of Patent: Mar. 18, 2003

(54) SELF-USE DENTAL INSTRUMENT

(76) Inventor: Ronald A. Mondi, 7 Sanborn St., Reading, MA (US) 01867

( * ) Notice: Subject to any disclaimer, the term of this patent is extended or adjusted under 35 U.S.C. 154(b) by 0 days.

(21) Appl. No.: 09/603,989

(22) Filed: Jun. 26, 2000

(51) Int. Cl.⁷ .................................................. A61C 3/06
(52) U.S. Cl. ..................................................... 433/142
(58) Field of Search .................... 433/142, 75; 401/49; 428/397

(56) References Cited

U.S. PATENT DOCUMENTS

| | | | | |
|---|---|---|---|---|
| 1,819,004 A | * | 8/1931 | Roessinger | 132/73 |
| 1,982,285 A | * | 11/1934 | Bronner | 433/142 |
| 2,011,270 A | * | 8/1935 | Chesler | 428/397 |
| 2,419,746 A | * | 4/1947 | Veria | 15/105.51 |
| 3,959,881 A | | 6/1976 | Kokal, Jr. | |
| 4,183,139 A | | 1/1980 | Tanaka | |
| 4,274,826 A | * | 6/1981 | Huey et al. | 433/142 |
| 4,547,155 A | | 10/1985 | Adler | |
| 4,571,184 A | | 2/1986 | Edwardson | |
| 4,780,083 A | * | 10/1988 | Croll | 438/216 |
| 5,273,425 A | | 12/1993 | Hoagland | |

* cited by examiner

Primary Examiner—John J. Wilson
Assistant Examiner—Melba Bumgarner
(74) Attorney, Agent, or Firm—Norman B. Rainer

(57) ABSTRACT

An inexpensive instrument for locating and remediating sites of a removable dental appliance causing sore spots on the wearer's gums includes a rigid shaft handle elongated between first and second extremities. Pigment which is transferrable by water is disposed at the first extremity. An abrading member is associated with the second extremity, and is shaped so as to have flat and round surfaces.

3 Claims, 1 Drawing Sheet

SELF-USE DENTAL INSTRUMENT

BACKGROUND OF THE INVENTION

1. Field of the Invention

This invention concerns an instrument useable by a dental patient to correct troublesome surfaces of his or her denture, partial denture or other oral appliance.

2. Description of the Prior Art

In the field of restorative dentistry, it is often necessary to find the "high spots" or premature contact sites between upper and lower teeth because said high spots interfere with the proper meshing or "occlusion" of upper and lower teeth. To find the high spots, the dentist usually applies a thin tape which leaves a mark on the high spot when the patient bites down. The high spot is then reduced by the usual dental abrasive tools acting upon the offending natural or artificial teeth, crowns or fillings.

Removable dental appliances such as a multi-tooth partial bridge or full denture have a trough-like gripping surface configured to rest against the patient's gums, palate or other portions of the oral cavity. In the case of newly made or newly re-lined removable appliances, it often happens that sore spots will develop where the gripping surface is too high. To remediate this problem, a dentist may have to spend considerable time in repeated patient visits to locate the site of the appliance which causes the sore spot, and abrading it to a lower profile. In such situation, the aforesaid techniques for remediating occlusional problems cannot be applied. It is further to be noted that sore spots may occur when it is inconvenient to see a dentist, such as at night or on weekends, holidays or when away on vacation.

It is accordingly an object of the present invention to provide an instrument which can be employed by a dental patient to locate and remediate sites of a dental appliance that cause sore spots.

It is a further object of this invention to provide an instrument as in the foregoing object which can be easily and safely utilized by the dental patient.

It is another object of the present invention to provide an instrument of the aforesaid nature of simple, durable construction amenable to low cost manufacture.

These objects and other objects and advantages of the invention will be apparent from the following description.

SUMMARY OF THE INVENTION

The above and other beneficial objects and advantages are accomplished in accordance with the present invention by an instrument for locating and remediating sites of a removable dental appliance which cause sore spots, said instrument comprising:

a) a rigid shaft handle elongated between first and second extremities, b) marking means associated with said first extremity, and c) abrading means associated with said second extremity.

BRIEF DESCRIPTION OF THE DRAWING

For a fuller understanding of the nature and objects of the invention, reference should be had to the following detailed description taken in connection with the accompanying drawing forming a part of this specification and in which similar numerals of reference indicate corresponding parts in all the figures of the drawing.

DESCRIPTION OF THE PREFERRED EMBODIMENT

Figure 1:
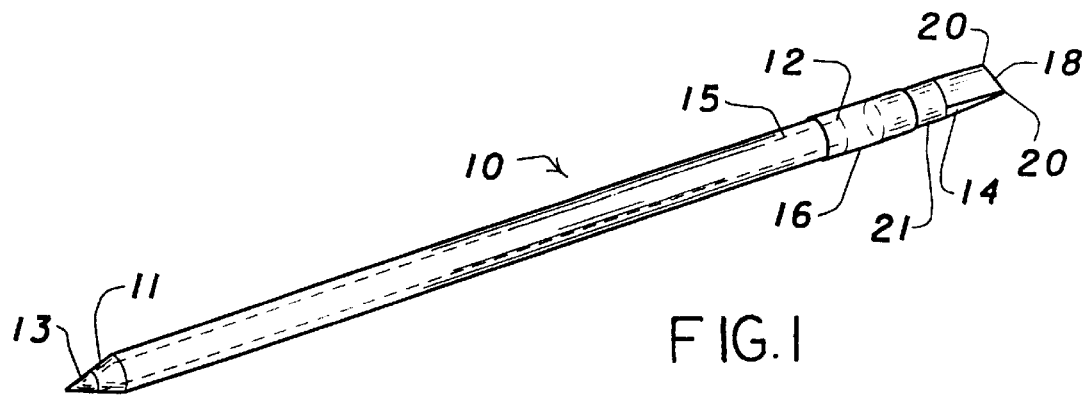
FIG. 1 is a perspective side view of an embodiment of the instrument of the present invention.
Figure 2:
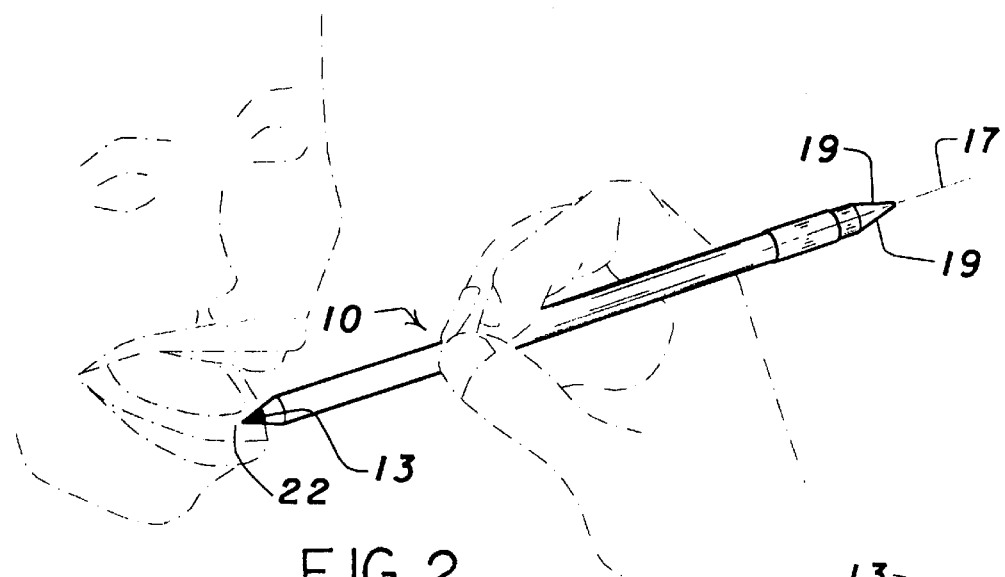
FIG. 2 is a side view of the embodiment of FIG. 1 rotated 90 degrees and shown in the course of actual use in marking a sore spot on the user's gum.
Figure 3:
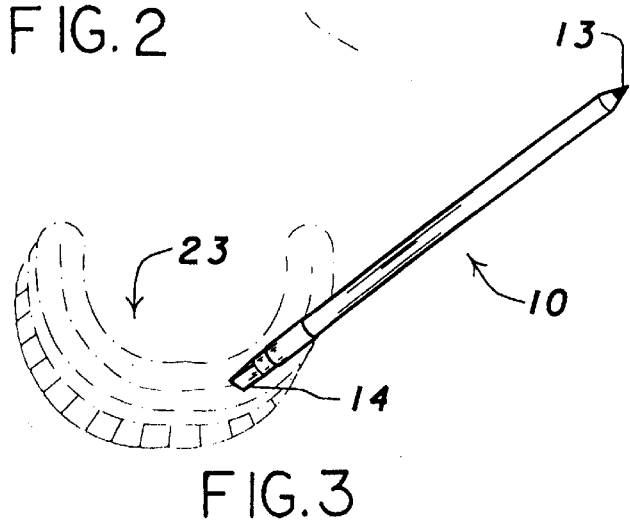
FIG. 3 is a side view of the embodiment of FIG. 1 shown in the course of actual use in abrading a site of a denture corresponding to the marked sore spot.

Referring to FIGS. 1–3, an embodiment of a dental instrument of the present invention is shown comprised of rigid shaft handle 10 elongated upon straight axis 17 between first and second extremities 11 and 12, respectively, said first extremity having marking means 13, and said second extremity having abrading means 14.

Handle 10 may have a length between about 3 and 7 inches, and is fabricated preferably of wood. In a particularly preferred embodiment, the handle is in fact a water color-type pencil having a central core 15 of a pigment which is transferable by water. Accordingly, the diametric configuration of the handle is uniform throughout its length, having a circular or polyhedral shape and diameter between about 6 and 9 millimeters. Said first extremity is conically pointed, as by way of a pencil sharpener, which exposes the central core as said marking means 13.

A metal sleeve 16 is preferably affixed to said second extremity 12. Abrading means 14 is secured by said sleeve in coaxial alignment with handle 10. Said abrading means is preferably a monolithic structure fabricated from a circular cylindrical rod of rigid abrasive composition. The abrading means preferably has two flat faces 19 symmetrically convergent with respect to axis 17 to form a straight chisel-type edge 18. Such configuration of the abrading means consequently has a variety of surface features, namely straight edge 18 with attendant corners 20, flat faces 19, and round surface 21. Such variety of surface features provide considerable versatility for accurately contacting and abrading high spots on a removable denture.

In use, when the denture wearer feels a pain on his gums under his new denture, he removes the denture, wets either his gums or the marking tip 13, and touches said tip to the site of pain 22, an action which deposits pigment at said site. He then re-inserts the denture and applies pressure for several seconds. Such action causes the pigment to accurately transfer from the gum to the denture, thereby defining the high spot. The abrading means is then utilized in a rubbing action to reduce the high spot.

The instrument of this invention is intended as a "giveaway" item to be handed out by dentists to the patient at the time of delivery of the denture and initial fitting thereof. Because the patient can utilize the instrument himself at home or on vacation, it eliminates the inconvenience of follow-up appointments with the dentist. It also saves the dentist numerous follow-up visits to adjust something for which he has already been paid. Accordingly, the dentist will prefer the minor expense involved in giving away an instrument of the present invention, instead of wasting valuable "chair" time in his office.

While particular examples of the present invention have been shown and described, it is apparent that changes and modifications may be made therein without departing from the invention in its broadest aspects. The aim of the appended claims, therefore, is to cover all such changes and modifications as fall within the true spirit and scope of the invention.

Having thus described my invention, what is claimed is:

1. An instrument for locating and remediating sites of a removable dental appliance causing sore spots, said instrument comprising:
   a) a rigid shaft handle elongated upon a straight axis between first and second extremities defining a length between 3 and 7 inches, said handle being fabricated of wood of uniform diametric configuration throughout said length and having a central core of a pigment which is transferable by water, said first extremity being conically pointed,
   b) marking means comprised of said central core of pigment located at said conically pointed first extremity, and
   c) abrading means secured by way of a sleeve to said second extremity and having two flat surfaces symmetrically convergent with respect to said axis to form a straight edge having attendant corners.

2. The instrument of claim 1 wherein said diametric configuration is selected from the group consisting of circular and polyhedral, having a diameter between about 6 and 9 millimeters.

3. The instrument of claim 1 wherein said abrading means is a monolithic structure fabricated from a circular cylindrical rod of abrasive composition.

* * * * *